United States Patent [19]

Cox et al.

[11] 4,154,827

[45] May 15, 1979

[54] INHIBITION OF ADH-STIMULATED OSMOTIC WATER FLOW AND ALDOSTERONE-STIMULATED SODIUM TRANSPORT

[75] Inventors: Malcolm Cox; Irwin Singer, both of Philadelphia, Pa.

[73] Assignee: University of Pennsylvania, Philadelphia, Pa.

[21] Appl. No.: 860,837

[22] Filed: Dec. 15, 1977

[51] Int. Cl.$^2$ .............................................. A61K 31/65
[52] U.S. Cl. .................................................. 424/227
[58] Field of Search ........................................ 424/227

[56] References Cited

PUBLICATIONS

Feldman et al., J. of Pharm. and Experimental Therapeutics, vol. 190, No. 2, pp. 358-364, 1974.

*Primary Examiner*—Jerome D. Goldberg
*Attorney, Agent, or Firm*—Holman & Stern

[57] ABSTRACT

Inhibition of ADH-Stimulated osmotic water flow employing anhydro-7-chloro-6-demethyltetracycline (ADC) is disclosed. Also disclosed is the use of ADC in the inhibition of aldosterone-stimulated sodium transport.

3 Claims, No Drawings

INHIBITION OF ADH-STIMULATED OSMOTIC WATER FLOW AND ALDOSTERONE-STIMULATED SODIUM TRANSPORT

BACKGROUND AND SUMMARY OF THE INVENTION

The invention described herein was made in the course of work under a grant or award from the Department of Health, Education and Welfare.

The present invention is concerned with inhibition of antidiuretic hormone (ADH)-stimulated osmotic water flow. More particularly, the present invention is concerned with the diuretic effects of anhydro-7-chloro-6-demethyltetracycline (ADC), as shown by the use of the compound in the inhibition of ADH-stimulated osmotic water flow. In addition, the present invention is concerned with the use of ADC in the inhibition of aldosterone-stimulated sodium transport.

Various studies have been reported in the prior art with regard to ADH-induced osmotic water flow, as well as with regard to the comparative effects of various tetracyclines on such water flow. Such studies are reported, for example, in: *Annals of Internal Medicine*, Vol 79, No. 5, 679–683 (Nov. 1973); *Journal of Pharmacology and Experimental Therapeutics*, Vol. 190, No. 2, 358–364 (1974); and *Annals of Internal Medicine*, Vol. 83, No. 5, 654–656 (Nov. 1975).

By the present invention there is provided an improved method for the inhibition of ADH-stimulated osmotic water flow. The method of the present invention includes the use as the inhibitor, the tetracycline, ADC.

As a further aspect of the present invention, the use of ADC in the inhibition of aldosterone-stimulated sodium transport is disclosed.

DESCRIPTION OF THE PREFERRED EMBODIMENTS

Demeclocycline (DMC) is known to cause nephrogenic diabetes insipidus in man and has been used successfully to treat the chronic hyponatremia associated with the syndrome of excessive ADH secretion (SIADH). DMC, but not oxytetracycline (OTC), also inhibits ADH-stimulated osmotic water flow in toad urinary bladders (a classical model of the mammalian distal nephron).

In accordance with the present invention, the effects of three tetracyclines: DMC, OTC and a new, non-antibacterial tetracycline, anhydro-7-chloro-6-demethyltetracycline (ADC), on ADH-stimulated osmotic water flow were investigated in in vitro studies employing toad urinary bladders.

The compound, anhydro-7-chloro-6-demethyltetracycline, which is employed in accordance with the present invention, may be prepared from 7-chloro-6-demethyltetracycline.HCl, the preparation of which is described in U.S. Pat. No. 2,878,289, incorporated herein by reference. Thus the desired compound may be prepared by the procedure as outlined in Example 1.

EXAMPLE 1

An amount of 100 g. of 7-chloro-6-demethyltetracycline.HCl was added to 2 liters of concentrated HCl with stirring in a heavy walled pyrex jar on a hot plate, and the mixture was heated for about 60 min. to a temperature of 81° C. Stirring was continued at the 81° C. temperature for about 25 minutes until all the solid material had dissolved. Precipitate began to form after about 15 minutes at this temperature.

The temperature of the solution was reduced to about 75° C. and there was then slowly added over a 25 minute period an amount of 2000 ml. of 2-butanol using a separatory funnel. The temperature dropped to 65° C. during the addition. Heat was applied to increase the temperature to 70° C. and the mixture was stirred for an additional 30 minutes. Heating was then discontinued and, with stirring, the mixture was allowed to cool gradually. Stirring was continued overnight for a total of 21 hours.

Next the crystals which had collected were filtered off on a 2000 ml. sintered glass funnel by a slow filtration which required about 5 hours. The crystals were washed with a 200 ml portion of 2-butanol (slurry in funnel) and then with a 300 ml portion of 2-butanol (slurry in beaker). The crystals were then vacuum dried in the funnel overnight. The product, anhydro-7-chloro-6-demethyltetracycline was obtained in the amount of 85 g.

The anhydro-7-chloro-6-demethyltetracycline product was recrystallized by a process which included adding 79 g. of anhydro-7-chloro-6-demethyltetracycline to a mixture of 1065 ml. butanol, 355 ml. ethyl Cellosolve and 119 ml. water in a 3 l. beaker, along with 95 ml. triethanolamine. The mixture was stirred and heated to 40°–44° C. until all the solid material had dissolved. The solution was then filtered on a 600 ml. sintered glass funnel with a Celite precoat.

The filtrate was transferred to a 3 l. beaker, heated to 45° C. and 69 ml. conc. HCl was added dropwise with overhead stirring during a 2 hr. period.

The mixture was next slowly filtered on a 600 ml. sintered glass funnel over a 5 hr. period and a vacuum was applied overnight. The crystals were then washed with 160 ml. of a 3:1 mixture of butanol and Cellosolve and a vacuum was applied for about 3 hours. The crystals were next dried in a vacuum oven for 24 hrs. at 48° C. The dried solid material was then ground up and washed on another funnel with 230 ml. of isopropyl alcohol (slurried). The washed product was then dried overnight at 48° C. for 20 hours in a vacuum oven. The product was then ground up and redried at 40° C. for 18 hrs. The recrystallized product, anhydro-7-chloro-6-demethyltetracycline, was obtained in an amount of 64.8 g.

In measuring the inhibition of ADH-stimulated osmotic water flow, paired hemibladders from a single toad provided control (C) and experimental (E) preparations in which ADH-stimulated osmotic water flow, at an ADH concentration of 100 mU/ml, was measured gravimetrically. The gravimetric procedures followed were similar to the procedures as set forth by Bentley, P. J. in *J. Endocrin.* 17, 201–209 (1958), incorporated herein by reference. Stock solutions of the tetracyclines were prepared in dimethylsulfoxide solvent, at a concentration of 250 mg/ml. Different sets of hemibladders were used for each tetracycline. The final serosal drug concentration in each case was 0.5 mg/ml of Ringer's solution. For each set of experiments, n=4–9. The results of the investigations are shown in Table I.

TABLE I

| | Medium pH = 7.9 | | |
|---|---|---|---|
| | Water Flow (ml/hr) | | % |
| Drug | E | C | Inhib |

TABLE I-continued

| Drug | E | C | % Inhib |
|---|---|---|---|
| DMC | 1.61±0.09 | 1.70±0.08 | −5.3 |
| OTC | 1.71±0.08 | 1.67±0.08 | +2.0 |
| ADC | 1.58±0.12 | 2.06±0.05 | −23.4* |

| Medium pH = 7.3 | | | |
|---|---|---|---|
| | Water Flow (ml/hr) | | % |
| Drug | E | C | Inhib |
| DMC | 1.28±0.11 | 1.68±0.08 | −23.6* |
| OTC | 1.66±0.08 | 1.78±0.08 | −6.7 |
| ADC | 0.33±0.02 | 1.96±0.04 | −83.2* |

*$p < 0.05$ or better

From the results as shown in Table I, it is seen that the inhibition of ADH-stimulated osmotic water flow in toad urinary bladders is pH dependent. This may be due to pH-induced changes in drug-protein binding and/or drug-lipid solubility. It is further noted that the antibacterial activity of tetracyclines is not essential for their effect on water transport. In addition, the results lead to the conclusion that the potential exists for the development of new tetracyclines which are more effective in the treatment of SIADH and other disorders of water homeostasis than DMC, and which lack the side effects of the latter drug.

With regard to the activity of ADC, the data reveal that ADC is by far the most potent tetracycline of the three which were tested, as far as inhibition of ADH-stimulated osmotic water flow is concerned. ADC is some four fold more potent that DMC, the next most powerful agent.

As an additional aspect of the present invention, the effects of tetracyclines upon aldosterone-stimulated sodium transport were investigated.

It is known that demeclocycline (DMC) causes natriuresis in patients with cirrhosis or congestive heart failure, but not in normal patients. The effects of DMC, minocycline (MNC), oxytetracycline (OTC) and anhydro-7-chloro-6-demethyltetracycline (ADC) on basal- and aldosterone-induced sodium transport were studied in vitro in toad urinary bladders, employing the paired quarter-bladder technique. The general procedures followed were similar to the short-circuit current techniques for measuring sodium transport as set forth by Sharp and Leaf in *Nature*, vol. 202, No. 4938, 1185–1188 (June 20, 1964), incorporated herein by reference.

Two of the quarter-bladders received aldosterone at time zero, and two hours later two of the quarter-bladders received OTC, MNC, DMC or ADC. Stock solutions of the tetracyclines were prepared in dimethyl-sulfoxide solvent, at a concentration of 250 mg/ml. Different sets of bladders were used for each tetracycline studied and the final serosal drug concentration in each case was 0.5 mg/ml of Ringer's solution. The results obtained are shown in Table II, with n=6–7 for each drug.

TABLE II

| Drug | % Inhibitor of Aldosterone Response |
|---|---|
| OTC | − 8% |
| MNC | −16%* |
| DMC | −66%* |
| ADC | −45%* |

*$p < 0.05$ or better

In summary, ADC was found to be about as potent as demeclocycline with regard to inhibition of aldosterone-stimulated sodium transport.

It is thought that the invention and many of its attendant advantages will be understood from the foregoing description, and it will be apparent that various changes may be made in the methods as described herein without departing from the spirit and scope of the invention or sacrificing its material advantages, the forms hereinbefore described being merely preferred embodiments thereof.

The embodiments of the invention in which an exclusive property or privilege is claimed are defined as follows:

1. A method for the inhibition of anti-diuretic hormone-stimulated osmotic water flow in a mammal in need of such treatment, comprising treating said mammal with an effective amount of anhydro-7-chloro-6-demethyl tetracycline as the inhibitor.

2. The method of claim 1 wherein said anhydro-7-chloro-6-demethyltetracycline is employed at a concentration of 0.5 mg/ml.

3. The method of claim 2 wherein the method is carried out at a pH of about 7.3.

* * * * *